United States Patent [19]
Barbier et al.

[11] Patent Number: 5,337,756
[45] Date of Patent: Aug. 16, 1994

[54] BLOOD SAMPLING DEVICE WITH A VACUUM TUBE

[75] Inventors: Georges A. E. Barbier; Patrick R. P. P. Marquis, both of Caen; Yvon Binet, 7, rue Charles Longuet, Bieville, all of France

[73] Assignees: Sylvain Thuaudet; George Albert Eugene Barbier; Patrick Roger P. P. Marquis; Yvon Binet, all of France

[21] Appl. No.: 7,320

[22] Filed: Jan. 21, 1993

[30] Foreign Application Priority Data

Jan. 22, 1992 [FR] France .................. 92 00680

[51] Int. Cl.⁵ .................................. A61B 5/00
[52] U.S. Cl. .................................. 128/763; 604/198
[58] Field of Search ............. 128/760, 763, 764, 770; 604/195, 198

[56] References Cited

U.S. PATENT DOCUMENTS

| | | | |
|---|---|---|---|
| 4,758,231 | 7/1988 | Haber et al. | 604/198 |
| 4,774,964 | 10/1988 | Bonaldo | 128/763 |
| 4,813,426 | 3/1989 | Haber et al. | 128/763 |
| 4,840,185 | 6/1989 | Hernandez | 128/770 |
| 4,846,808 | 7/1989 | Haber et al. | 128/763 |
| 4,850,374 | 7/1989 | Diaz-Ramos | 128/770 |
| 4,892,107 | 1/1990 | Haber | 128/763 |
| 4,900,310 | 2/1990 | Ogle, II | 604/198 |
| 4,947,863 | 8/1990 | Haber et al. | 128/764 |
| 4,957,490 | 9/1990 | Byrne et al. | 604/197 |
| 5,030,209 | 7/1991 | Wanderer et al. | 604/198 |
| 5,086,780 | 2/1992 | Schmitt | 128/763 |

FOREIGN PATENT DOCUMENTS

| | | | |
|---|---|---|---|
| 2653668 | 5/1991 | France . | |
| 9106332 | 5/1991 | PCT Int'l Appl. | 128/764 |

*Primary Examiner*—Max Hindenburg
*Attorney, Agent, or Firm*—Seidel, Gonda, Lavorgna & Monaco

[57] ABSTRACT

A blood sampling device has a vacuum tube and a sleeve provided with a two-ended needle. When one end of the needle is placed in a vein in order to take a blood sample, a seal in the vacuum tube is perforated by the second end of the needle so as to create suction for taking a blood sample. The sleeve comprises a base with an outlet and guide aperture, and a tubular section for guiding and protecting the first end of the needle. The sleeve includes a guiding and locking groove with two locking positions. The locking positions consist of a longitudinal section corresponding substantially to the movement which the needle has to perform in order to pass from its retracted position into its operating position and terminating at each end in a locking extension which is transverse relative to the sliding direction and which corresponds to each of the two locking positions. The needle is provided with a guiding and locking disc placed in the sleeve and comprises at least one tab accommodated in the groove and accessible from the exterior of the sleeve. Accordingly, the sleeve can be passed manually from its locked retracted position into a locked operating position such that the needle is outside of the sleeve. The guiding and locking disc comprises a fastener on its rear face. The plug of the vacuum tube connects to the rear face of the guiding and locking disc.

6 Claims, 3 Drawing Sheets

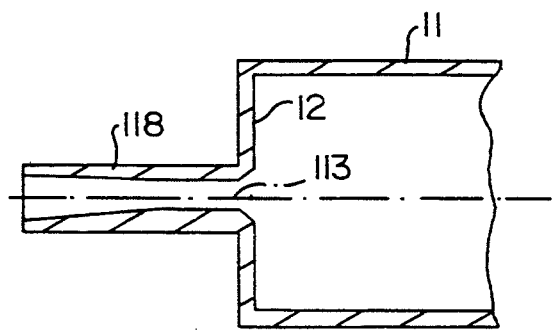
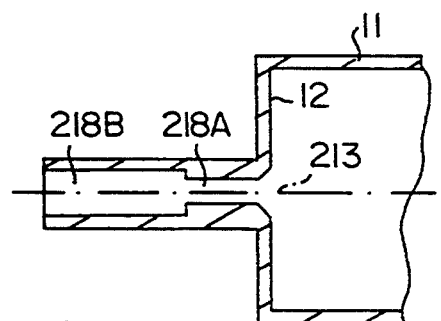
FIG. 6  FIG. 7
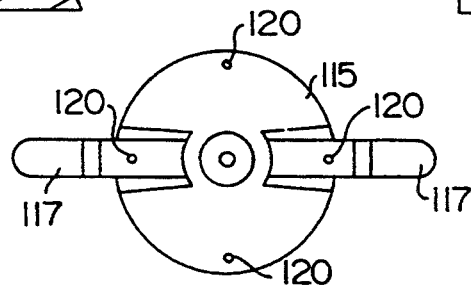
FIG. 8A
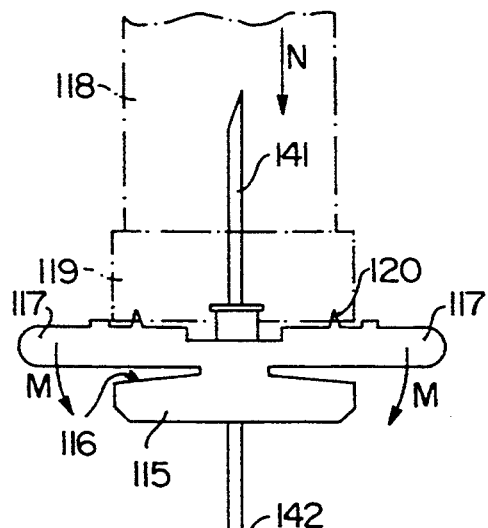
FIG. 8B
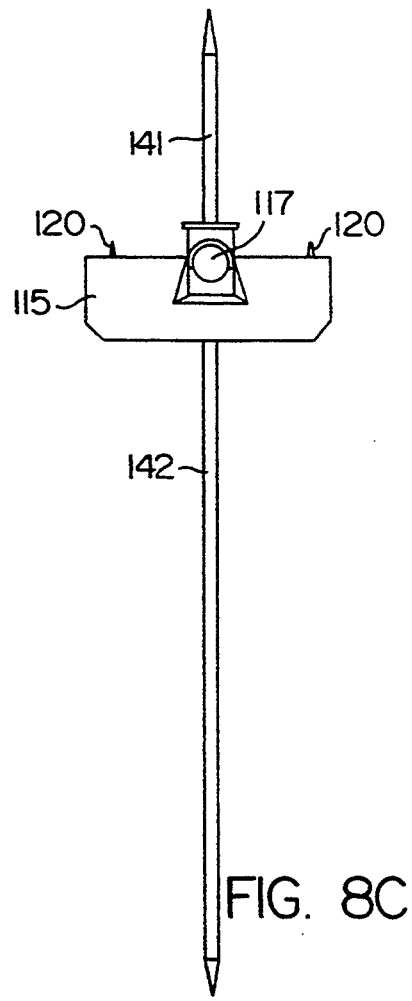
FIG. 8C

BLOOD SAMPLING DEVICE WITH A VACUUM TUBE

BACKGROUND OF THE INVENTION

The present invention relates to a blood sampling device with a vacuum tube of the type comprising a sleeve provided with a two-ended needle of which the first end is to be injected into the patient and the second end is to perforate the plug in the vacuum tube which is placed in the sleeve and which, when the first end has been placed in the vein to take the blood sample, is fitted onto the other end of the needle so as to create suction for taking the blood sample.

In order to take the blood sample, the tube is partially engaged in the sleeve but is prevented from being fitted onto the needle. The patient is then injected and the tube pressed down onto the needle so as to perforate its plug. The vacuum prevailing in the tube thus creates low pressure which draws the blood into the tube. At the end of this sampling step, the tube is extracted from the sleeve. The needle and sleeve may be left in place in order for a further sample to he taken from the same patient. If this is not desired, the needle is extracted and has to be fitted with a cap before disposal. The needle must then be unscrewed and a further cap fitted onto the rear part of the needle.

This operation requires a certain amount of cars and the user may possibly prick himself and thus risk contamination.

The aim of the present invention is to overcome these disadvantages and proposes creating a blood sampling device with a single-use vacuum tube which has a simple structure and provides particularly effective protection against all risk of injury by the needle.

To this end, the invention relates to a blood sampling device with a vacuum tube characterised by the means set out in the claims.

SUMMARY OF THE INVENTION

The disposable device according to the invention has the advantage of an extremely simple structure made of the same materials as the known device and thus eliminating all the problems involved in material compatibility. This device is far simpler than the known device since the needle no longer has to be placed in a cap and sterile packaging in order to be secured on the front end of the sleeve accommodating the vacuum tube. On the contrary, the assembly formed by the sleeve and the needle is already assembled which reduces the number of parts and consequently the cost. In view of the considerable number of such devices used daily in hospitals, this problem of reducing costs combined with a considerable improvement in safety when the device is used constitutes an extremely significant advance.

The device according to the invention is very easy to use and there is no risk of the user pricking himself at any moment when positioning the needle and in particular when withdrawing the needle, in particular since he is obliged to hold the sleeve of the device in one hand and the tube in the other in order to unlock then pull the guiding disc and thus the needle into its retracted position.

The operation is thus limited to action on parts which are relatively far away from the tip of the needle used to inject the patient and the fastening of the disc to the tube plug such that these two parts are rendered rotationally integral enables the unlocking and withdrawal movement of the needle to be performed at the end of the operation: as a result of the tube being rotated, the guiding disc is rotated (fastening between the tube plug and the pins), then as a result of pulling on the tube, the needle is drawn via its rear part thanks to the constriction of the rubber and the weight of the needle, the device being turned around for this operation (tip of the needle—at the patient end —turned upward). The needle and its guiding and locking part can be introduced during manufacture as a result of the resilience of its sleeve walls being altered in order to pass along the excess thickness represented by the tabs until they appear in the opening in the groove.

For this assembly it is also possible to provide a sleeve which is split at the rear such that the tabs can pass into the groove.

In accordance with a further feature, the sleeve comprises a second groove in a position which is diametrically opposite the axis of the sleeve and has a shape which is symmetrical relative to the axis of the sleeve.

Although the grooves and their corresponding tabs can be provided in asymmetrical positions which are not diametrically opposite, it is preferable if they are in order that the stresses are better distributed and the sliding movements facilitated.

The present invention will be described below in further detail with reference to the attached drawings.

BRIEF DESCRIPTION OF THE DRAWINGS

FIG. 6 is a section of a different embodiment of the front of the sleeve;

FIG. 7 is a section of a further different embodiment of the front of the sleeve;

FIGS. 8A, 8B and 8C show in plan, front and side view the disc provided with the needle according to a different embodiment.

DETAILED DESCRIPTION OF THE INVENTION

Figure 1:
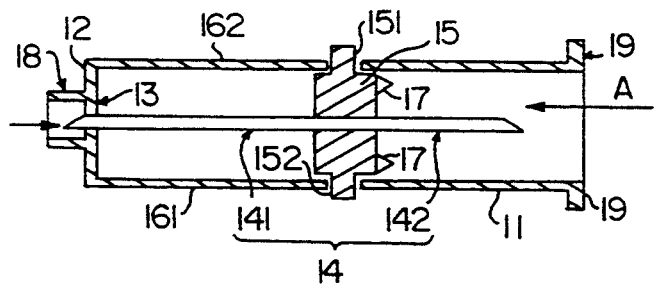
FIG. 1 is a diagrammatic view in section of a sleeve of the blood sampling device according to the invention.

In accordance with FIG. 1, the blood sampling device with a vacuum tube according to the invention, which is only shown in part, consists of a sleeve 11 of which the base 12 is provided with an aperture 13 for the passage and guiding of the needle 14.

The needle 14 has two ends 141, 142, the first end 141 being used to inject the patient and the second end 142 being used to perforate the plug of the vacuum tube introduced into the sleeve from the right hand side toward the left hand side as viewed in FIG. 1 (arrow A).

The needle 14 is provided with a guiding and locking disc 15 placed in the sleeve 11 and comprising two tabs 151, 152 which are accessible from the exterior of the sleeve 11 and are accommodated in grooves 161, 162 provided in the wall of the sleeve 11. As shown in FIG. 1, the tabs 151, 152 are diametrically opposite relative to the longitudinal axis of the sleeve 11, as are the grooves 161, 162 which accommodate them.

Figure 2A:
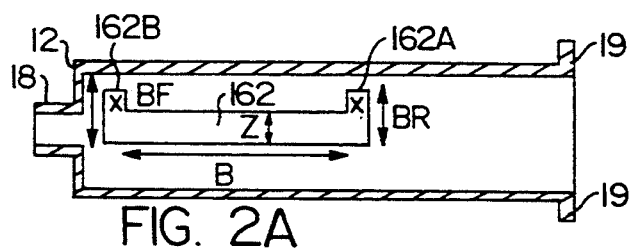
FIG. 2A shows the blood sampling sleeve alone in axial section.
Figure 2B:
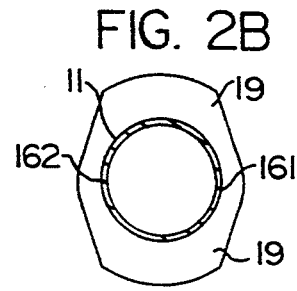
FIG. 2B is a view of the open end of the sleeve of FIG. 2A.

The plan view of FIG. 2A shows the shape of the groove 162.

As a result of the two tabs 151, 152 being acted upon, the needle 14 can thus be passed from the retracted position shown in FIG. 1 into the delivery position as a result of the assembly formed by the needle 14 and the guide disc 15 being advanced in its groove.

At each end of the groove 162 there is a locking position 16A, 162B enabling the disc 15 to be rotated about its axis represented by the needle as a result of the rotational movement of the disc 15. This movement is achieved by a transverse rotation along the axis of the needle (double arrow BR) enabling the tab 151 corresponding to this groove 162 to be passed either into the locking position 162A or in the groove 162 permitting the slide movement (double arrow B). The function of the locking position 162B at the other end of the groove 162 is to enable the tab 151 to be blocked when the needle 14 is in the operating position.

In the simplest case shown in FIG. 2A, the groove 162 comprises a longitudinal section connecting the two locking positions. This longitudinal section is parallel with the sleeve axis. This is only one particular embodiment, the advantage of which is its simplicity.

The division into two of the extension, i.e. the presence of the tab 152 in addition to the tab 151, enables the device to be produced symmetrically preventing the disc 15 from seizing under the force of translation.

At its rear the disc 15 comprises fastening means such as pins 17 or fastening bars in which the plug of the vacuum tube in injected or attached by its edge so as to be fastened to the part 15 and enable it to be released and withdrawn and completely released after use (placing of the tabs 152, 152 in the notches 162A), the needle being completely retracted in the tube at this moment.

The manoeuvre is performed very simply; it is sufficient for the blood sampling tube to be rotated about itself as a result of being held in one hand, the other hand holding the sleeve; the user then draws on the tube so as to withdraw the needle and retract it. Finally, the disc is locked in its end-of-travel position, and, as a result of greater stress being exerted, the tube is detached from the disc.

Advantageously, the tabs 151, 152 project slightly relative to the outer surface of the sleeve; the amount by which they project depends on ergonomics.

At the front the sleeve terminates in a tubular section 18 which protects the end of the section 141 of the needle projecting out of its aperture 13 when the needle is in the retracted position. This aperture 13 remains behind the sloping edge of the section 141 of the needle.

At the rear, the sleeve has two gripping lugs 19 which are also diametrically opposite one another.

Figure 3A:
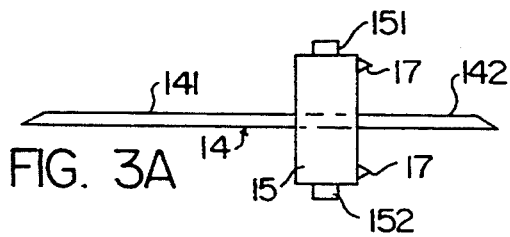
FIG. 3A shows the needle and its guiding part in side view.
Figure 3B:
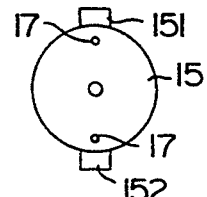
FIG. 3B is a view of the rear corresponding to FIG. 3A.

FIGS. 3A and 3B show the needle 14 and the guiding and locking part 15 outside the sleeve. FIG. 3B shows the particular shape of the tabs 151, 152 and the position of the pins 17.

Figure 4:
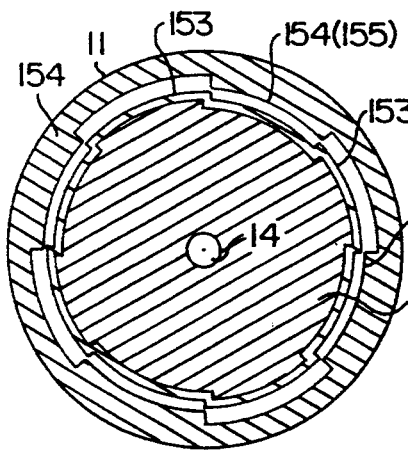
FIG. 4 is a view in section of a different embodiment of the sleeve and the needle guiding part.
Figure 5:
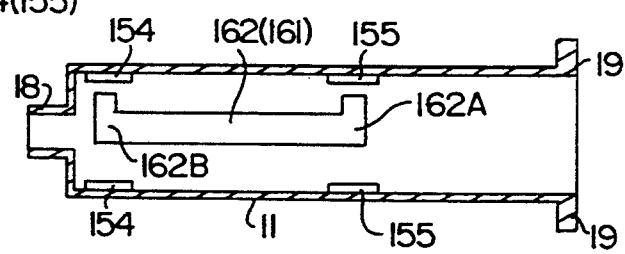
FIG. 5 is a view in axial section of the sleeve of FIG. 4.

In accordance with FIGS. 4 and 5 it is advantageous for the part 15 bearing the needle 14 to be completely locked in the first and second positions. For this purpose, the part 15 comprises projecting sections 153 (FIG. 4) for co-operating with sections 154, 155 in the form of tabs at the front and rear of the tube 11 in locations corresponding to the locking positions and projecting relative to the inner contour of the sleeve 11. When the sections 153 have passed between the section 154, 155, the part 15 is pivoted as described above and this pivoting causes the sections 153 to pass in front of the similar sections 154, 155. This bayonet-type fastening means completes the stage in which the device is locked in the position of use. The similar sections 154, 155 for locking it in the operating position and the retracted position are shown in FIG. 5.

The sections 153 and sections 154, 155 can also cooperate directly with one another in the manner of cams in so far as the shape of one of the sections 153 and/or 154, 155 is not exactly circular but widens out. There is thus a wedging or cam effect which stiffens the inverse rotational movement and preserves the locking effect either in the position of use or the retracted position.

The variant of the front wall according to Fig. 6 corresponds to a sleeve 118 which, on the interior, widens from the guide aperture 113, whilst, in the embodiment shown in FIG. 7, the sleeve 218 has a smaller drilling and a drilling with a larger diameter 218A, 218B in front of the guide aperture 213.

In accordance with FIGS. 8A, 8B, 8C, the guiding and locking disc 115 supporting the needle 14 (141, 142) has indentations 116 so as to enable the two tongues 117 constituting the locking tabs to be able to tilt backwards (arrow M) when a thrust is exerted in the direction of the arrow N by the tube 118 and its plug 119 on the tongues 117 so as to release the disc 115 in its front position.

The top of the disc 115 and of the tongues 117 supports fastening members 120 for example in the form of tips on which the plug 119 of the tube 118 connects.

Figure 9A:
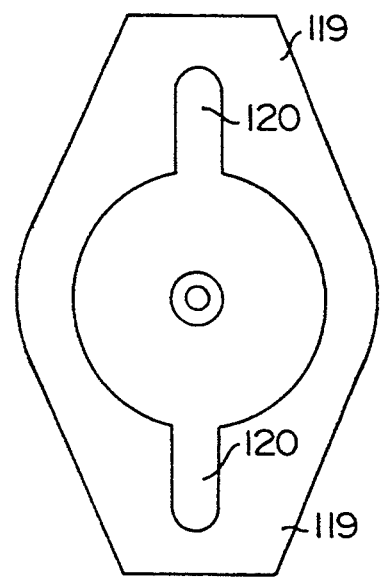
FIGS. 9A and 9B show a plan view and a view in axial section of the sleeve of the device.
Figure 9B:
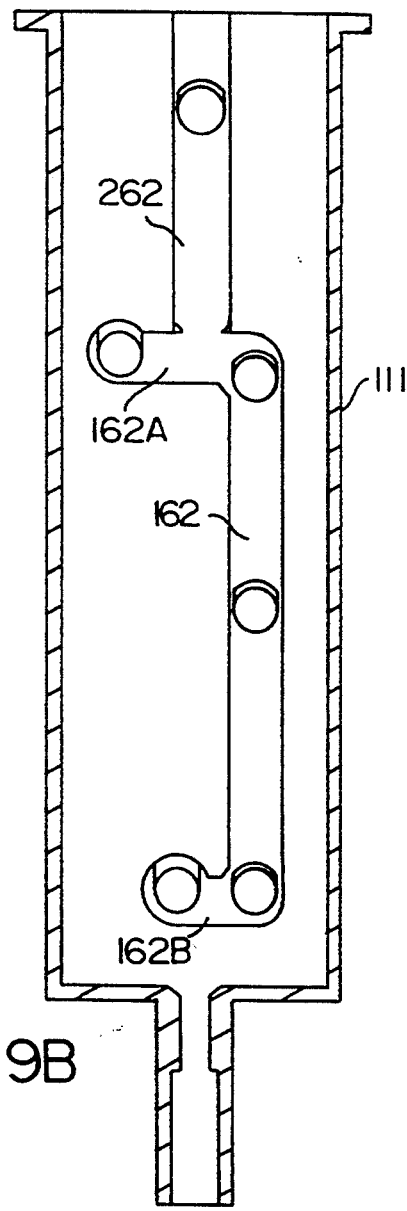

FIGS. 9A, 9B show a variant 111 of the sleeve 11 in FIG. 1. In accordance with this variant the groove 162 is extended beyond its section 162A by an assembly groove 262 which opens out behind the open rear of the sleeve 111; in order to enable the tabs 117 (FIG. 8B) to pass through, the lugs 119 are also provided with cut-outs 120. Thus, in order for the device to be assembled, the disc and its needle are slid from behind into the sleeve.

In a general manner, the various parts of the device have sufficient clearance between them such that the movements can be performed easily whilst permitting excellent fastening both in the operating and in the retracted positions.

What is claimed is:

1. A blood sampling device comprising a sleeve provided with a two-ended needle of which the first end is intended for injecting the patient and the second end is intended to perforate a plug of a vacuum tube placed in the sleeve and which, when the first end of the needle has been placed in the vein in order to take a blood sample, is connected onto the second end of the needle so as to create suction for taking a blood sample, wherein the sleeve comprises:

a) a base with an outlet and guide aperture at one end of a tubular section for guiding and protecting the first end of the needle;

a guiding and locking groove with two locking positions consisting of a longitudinal section having a length substantially equal to the distance which the needle must travel in order to pass from its retracted position into its operating position, the groove terminating at each end in a locking extension which is transverse relative to the axis of the tubular section and which corresponds to each of the two locking positions;

b) the needle being provided with a guiding and locking disc placed in the sleeve and comprising at least one tab received in the groove and accessible from the exterior of the sleeve such that the needle can be passed manually from its locked retracted position into a locked operating position such that the needle is outside the sleeve;

c) the guiding and locking disc comprising a fastening means on its rear face, onto which the plug of the vacuum tube connects.

2. The blood sampling device according to claim 1, wherein the sleeve further comprises a second groove positioned diametrically opposite the first groove relative to the axis of the sleeve and having a shape which is symmetrical relative to the axis of the sleeve, and the guiding and locking disc comprises a corresponding tab.

3. The blood sampling device according to claim 1, wherein the guiding and locking disc and the sleeve further comprise complementary means for locking the guiding and locking disc in position by the cam effect.

4. The blood sampling device according to claim 1, wherein the guiding and locking disc further comprises indentations and the locking tabs consist of tongues which, under the effect of the thrust exerted on a blood sampling tube, can withdraw resiliently into the indentations so as to unlock.

5. The blood sampling device according to claim 1, wherein the groove is extended by an assembly groove for introducing the disc and needle into the sleeve.

6. The blood sampling device according to claim 1 wherein the guiding and locking disc and sleeve further comprise complementary means for locking the guiding and locking disc in position by a bayonet-type connection.

* * * * *